United States Patent [19]
Kleemiss et al.

[11] Patent Number: 6,107,522
[45] Date of Patent: Aug. 22, 2000

[54] PROCESS FOR THE PREPARATION OF CYCLOPROPYLAMINE

[75] Inventors: Wolfgang Kleemiss, Haltern; Marcel Feld, Cologne; Manfred Kaufhold, Marl, all of Germany

[73] Assignee: Degussa-Huels Aktiengesellschaft, Frankfurt, Germany

[21] Appl. No.: 09/350,289

[22] Filed: Jul. 9, 1999

[30] Foreign Application Priority Data

Jul. 9, 1998 [DE] Germany ............................ 198 30 633

[51] Int. Cl.$^7$ .................................................. C07L 209/00
[52] U.S. Cl. .............................................................. 564/446
[58] Field of Search ............................................... 564/446

[56] References Cited

FOREIGN PATENT DOCUMENTS 1257097  12/1971  United Kingdom .

*Primary Examiner*—Paul J. Killos
*Attorney, Agent, or Firm*—Oblon, Spivak, McClelland, Maier & Neustadt, P.C.

[57] ABSTRACT

Cyclopropylamine is prepared from butyrolactone by a process comprising:

(a) reacting butyrolactone with hydrogen chloride, thereby yielding chlorobutyric acid, (b) esterifying said chlorobutyric acid with a primary or secondary alcohol having 4–8 carbon atoms, (c) cyclizing the ester with an alkali metal alcoholate of a primary alcohol having 1–3 carbon atoms to give a mixture of cyclopropanecarboxylic acid esters, (d) converting the cyclopropanecarboxylic acid ester mixture into cyclopropanecarboxylic acid amide by reacting the ester mixture with ammonia, and (e) reacting said cyclopropanecarboxylic acid amide with hypohalite ion in a basic medium, thereby forming cyclopropylamine.

13 Claims, No Drawings

PROCESS FOR THE PREPARATION OF CYCLOPROPYLAMINE

BACKGROUND OF THE INVENTION

Field of the Invention

The present invention relates to a process for the preparation of cyeclopropylamine from γ-butyrolactone (hereinafter identified as "butyrolactone"). More particularly, the invention relates to the stage of a process in which a γ-chlorobutyric acid ester ("chlorobutyric acid ester") is cyclized to a cyclopropanecarboxylic acid ester.

Cyclopropylamine is an important precursor for the synthesis of pharmaceuticals and agricultural chemicals. An inexpensive method of preparing the compound is, therefore, desirable. Cyclopropylamine is usually prepared from γ-butyrolactone via the intermediate stages of γ-chlorobutyric acid ("chlorobutyric acid"), chlorobutyric acid ester, cyclopropanecarboxylic acid ester and cyclopropanecarboxylic acid amide. This reaction sequence and individual intermediate stages have been described in several instances. It is thus known that cyclopropanecarboxylic acid ethyl ester can be prepared by cyclization of chlorobutyric acid ethyl ester with sodium t-amylate as the cyclizing base, the yield being only 45% (Julia et al, Bull. Soc. Chim. France 1960, 306 et seq.). A yield of 66% which was achieved in the preparation of cyclopropanecarboxylic acid ethyl ester by reaction of chlorobutyric acid ethyl ester with sodium methylate (Bunce et al., Organic Preparations and Procedures 6, 193–6 [1969]) is also unsatisfactory.

The five-stage reaction sequence mentioned for the preparation of cyclopropylamine in the form of an aqueous solution is described, for example, in U.S. Pat. No. 3,711, 549 or DE 19 39 759. In this process, butyrolactone is first converted with hydrogen chloride into chlorobutyric acid, which is subsequently or simultaneously esterified with a lower alkanol to give the chlorobutyric acid alkyl ester. The ester is then cyclized in the presence of an inert solvent such as toluene, to the cyclopropanecarboxylic acid ester, which then reacts with ammonia in the reaction mixture under base catalysis to give cyclopropanecarboxylic acid amide, which is finally degraded to cyclopropylamine in a Hofmann reaction. In the texts of the patents, only the methylate is mentioned as the chlorobutyric acid ester and only sodium methylate is mentioned as the base for the cyclization. The overall yield of cyclopropylamine, based on chlorobutyric acid ester, is stated as 80%, and the yield in the cyclization step is stated as about 92%. A disadvantage of this process is that lower esters of chlorobutyric acid are more difficult to prepare than the esters of higher alcohols. This difference in ester preparation results from the fact that the water formed during the reaction can be discharged azeotropically from the reaction mixture and separated as a separate phase in the condensate only using higher alcohols. The addition of an inert, water-immiscible solvent for azeotropic removal of water leads to an increased expenditure upon distillation.

The process disclosed in EP 0 043 949, which comprises two intermediate stages, also has a similar disadvantage. In this process, chlorobutyric acid methyl or ethyl ester is cyclized with sodium methylate or potassium methylate in the presence of liquid ammonia in one step to give the cyclopropanecarboxylic acid methyl or ethyl ester. The ester is amidated. The yield of cyclopropanecarboxylic acid amide is indeed >90%. However, liquid ammonia is a substance which requires particular safety precautions when used. Furthermore, metering of liquid ammonia is more expensive in terms of apparatus than metering of ammonia in gaseous form.

According to EP 0 205 403, in a process for the preparation of cyclopropylamine starting from butyrolactone, chlorobutyric acid esters of secondary or tertiary alcohols are cyclized to a sterically hindered cyclopropanecarboxylic acid ester by means of solid sodium hydroxide in an inert solvent with the addition of a phase transfer catalyst. Esters of tertiary alcohols such as tert-butanol, gave the best results. Of the esters of secondary alcohols, the isopropyl and 2-butyl ester were mentioned. The yields are stated as >90%. However, in this case the chlorobutyric acid ester must be purified by distillation, which makes the process expensive, as does the use of phase transfer catalysts such as tributylmethylammonium chloride. Furthermore, the subsequent amidation step requires monosodium ethylene glycolate, which is relatively expensive to prepare. The yield of cyclopropylamine over all the stages is about 80%.

The intermediate stage in which a cyclopropanecarboxylic acid ester is converted into the amide has also already been described in several instances. Thus, according to EP 0 662 470, cyclopropanecarboxylic acid esters of lower alcohols having 1–3 carbon atoms are amidated using an alkali metal alcoholate of a monohydric alcohol having 1–8 carbon atoms as a catalyst. No inert solvent is necessary here to achieve good yields. However, the reaction is performed only up to an ester conversion of 60–90%, so that the reaction mixture can still be handled. After removal of the cyclopropane-carboxylic acid amide, the mother liquor, which still contains cyclopropanecarboxylic acid ester, can be recycled to the amidation reaction, so that the yields of >90% are finally achieved. This process is advantageous only if cyclopropanecarboxylic acid esters of lower alcohols having 1–3 carbon atoms are favorably available.

The process disclosed in EP-B1 0 365 970 also leads from cyclopropanecarboxylic acid ester to cyclopropanecarboxylic acid amide. An ester of a $C_4$- to $C_8$-alcohol is employed, an alkali metal alcoholate of a $C_1$- to $C_8$-alcohol is used, and the process is operated with gaseous ammonia. The yields here are >95%. A particularly preferred ester is the isopropyl ester, no information being given as to its preparation. The space/time yield of the process is low, since cyclopropanecarboxylic acid esters of higher alcohols have a relatively high molecular weight, while cyclopropanecarboxylic acid amide has a comparatively low molecular weight.

The Hofmann degradation of cyclopropanecarboxylic acid amide to cyclopropylamine is described in three other patent specifications. On the one hand, the amide can be degraded continuously to the amine in solution either in a temperature range of from 10–35° C. (EP 0 367 010) or of from 45–260° C. (EP 0 393 350). On the other hand, the degradation takes place semi-continuously in suspension if, after prechlorination of the amide, which proceeds at a low temperature, the then homogeneous solution is passed continuously through a tube reactor at elevated temperature (DE 195 23 868.0). In all cases, yields of cyclopropylamine of >90%, based on the amide employed, are obtained. A prerequisite of the processes mentioned is the availability of pure cyclopropanecarboxylic acid amide, which must be prepared by the very expensive routes described above.

In spite of the numerous proposals of synthesis, a need continues to exist for an improved process for the preparation of cyclopropylamine starting from butyrolactone which gives a high overall yield and high space/time yields, operates with readily accessible catalysts and occurs without the presence of inert solvents. In particular, a need continues to exist for an improved cyclization reaction which can be used in the process mentioned and starts from readily available chlorobutyric acid esters.

SUMMARY OF THE INVENTION

Accordingly, one object of the present invention is to provide an improved cyclopropylamine synthesis process and, in particular, an improved cyclization reaction of the overall synthesis.

Briefly, this object and other objects of the present invention as hereinafter will become more readily apparent can be attained by a process for the preparation of cyclopropylamine from butyrolactone, comprising:

(a) reacting butyrolactone with hydrogen chloride, thereby yielding chlorobutyric acid;

(b) esterifying said chlorobutyric acid with a primary or secondary alcohol having 4–8 carbon atoms;

(c) cyclizing the ester with an alkali metal alcoholate of a primary alcohol having 1–3 carbon atoms to give a mixture of cyclopropanecarboxylic acid esters;

(d) converting the cyclopropanecarboxylic acid ester mixture into cyclopropanecarboxylic acid amide by reacting the ester mixture with ammonia; and (e) reacting said cyclopropanecarboxylic acid amide with hypohalite ion in a basic medium, thereby forming cyclopropylamine.

DETAILED DESCRIPTION OF THE PREFERRED EMBODIMENTS

The cyclization stage (c) of the present process achieves the important objective of providing an improved cyclization reaction.

The overall process yields cyclopropylamine having a purity of >98% in yields of about 70%, based on butyrolactone. In stage (c), the cyclopropanecarboxylic acid esters are obtained in a yield of about 90%, based on the chlorobutyric acid ester.

Stage (a) is conducted, for example, by reacting butyrolactone with dry hydrogen chloride in a manner known per se at a temperature which expediently does not exceed 135–140° C. under a pressure of up to 25 bar and as a rule without a catalyst, in an initially highly exothermic reaction.

In stage (b), chlorobutyric acid is expediently esterified as the crude product, which contains γ-(γ-chlorobutyryl)butyric acid as a by-product, with a primary or secondary alcohol having 4–8 carbon atoms. In contrast to the esters of lower alcohols, these esters are easy to prepare. Preferred esterifying alcohols include primary alkanols, for example, 1-butanol, 1-pentanol and 1-hexanol. Secondary alkanols such as 2-butanol, 2- or 3-pentanol and 2- or 3-hexanol are also particularly suitable. Processes of esterification using primary or secondary alcohols are well-known. The reaction is conducted, e.g. at temperatures from 120–140° C. without a catalyst.

Stages (a) and (b) can also be combined by introducing hydrogen chloride and the alcohol simultaneously into the butyrolactone which has been initially introduced into the reaction vessel.

Stage (c) is an essential part of the overall process. In this stage, the chlorobutyric acid ester from stage (b) is cyclized. An alkali metal alcoholate, advantageously a sodium alcoholate, of an alcohol, expediently an alkanol having 1–3 carbon atoms, is used for the reaction. The preferred alkali metal alcoholate is sodium methylate, which is readily accessible in industrial quantities. The alkali metal alcoholate is expediently used as a solution in the corresponding alcohol, and expediently employed in amounts of 1–1.5 equivalents per equivalent of chlorobutyric acid ester. The cyclization can be effected without addition of an additional inert solvent by initially introducing the alcohol/alcoholate solution into the reaction vessel at a temperature which is advantageously 80–150° C. If desired or necessary, some or all of the alcohol used as solvent for the alcoholate is removed by distillation and the crude chlorobutyric acid ester is metered in while stirring. Alcohol employed as the solvent and formed by transesterification from the carboxylic ester function can also be removed by distillation during the reaction.

The reaction product is a mixture of cyclopropanecarboxylic acid esters which contain the original carboxylic ester function and a carboxylic ester function which has an alcohol component, is formed by transesterification and originates from the solvent, used as the alcohol, for the alcoholate. The mixture can be used in the subsequent stage without further work-up.

In stage (d), the cyclopropanecarboxylic acid ester mixture of stage (c) is converted into cyclopropanecarboxylic acid amide. The reaction of this stage can be effected by one of the processes described in the prior art. For example, in one procedure, the ester mixture is reacted with ammonia at a temperature of 40–120° C., preferably 60–80° C., under a pressure of 1.0–5.0 bar. The reaction proceeds astonishingly smoothly, although the educt is an ester mixture.

The overall process also does not differ in principle from the corresponding processss of the prior art with respect to stage (e). Thus, a suspension or a solution of the crude cyclopropanecarboxylic acid amide in water, with or without prior removal of residual organic solvents, can be subjected to Hofmann degradation. The hypohalite, preferably sodium hypochlorite, is advantageously employed in amounts of 1.0–1.5 equivalents, in particular 1.0–1.2 equivalents, and the base, preferably sodium hydroxide, is advantageously employed in amounts of 1.5–2.5 equivalents, in particular 1.8–2.2 equivalents, in each case based on the carboxamide function, and the reaction is in general conducted at temperatures from 40–150° C., in particular from 60–80° C.

Having now generally described the invention, a further understanding can be obtained by reference to certain specific Examples which are provided herein for purpose of illustration only and are not intended to be limiting unless otherwise specified.

EXAMPLES

Example 1

Stages (a) and (b): 86.1 g (1.0 mol.) of butyrolactone are heated to a temperature of 135° C., while stirring. 80.0 g (1.07 mol.) of n-butanol and an excess of gaseous hydrogen chloride are metered in over a period of 4.5 hours, a temperature of 130–135° C. being maintained. During the reaction, 124.0 g of distillate are removed. The reaction mixture is then freed of excess n-butanol at about 70° C. under a pressure of 60 mbar. A residue of 211.2 g remains.

Stage (c): Methanol is removed from 225.0 g (1.25 mol.) of 30% strength by weight methanolic sodium methylate solution by distillation up to a bottom temperature of 100° C. The crude chlorobutyric acid butyl ester from stages (a) and (b) is then metered in over a period of 1.5 hours. During this operation, a temperature of 97–100° C. is maintained in the reaction mixture, while a mixture of methanol and n-butanol is removed by distillation continuously. When the metering has ended, the mixture is kept at a bottom temperature of about 100° C. for a further 2 hours.

Stage (d): The reaction mixture of stage (c) is cooled to 60° C. and reacted with an excess of gaseous ammonia under normal pressure. The reaction time is about 10 hours. After cooling to room temperature, the reaction mixture is rendered neutral with 80.0 g of 20% strength by weight hydrochloric acid. Solvent residues are removed by distillation over a column having a bottom temperature of up to 120° C. The mixture is allowed to cool and water is added in an amount such that a homogeneous solution (659.4 g) forms. According to HPLC analysis, the cyclopropanecarboxylic acid amide is present in a yield of 70%, based on the butyrolactone.

Stage (e): 160.0 g (2.0 mol.) of 50% strength by weight sodium hydroxide solution are added at 0° C. to the solution from stage (d) and the mixture is heated to about 15° C. 1010.9 g (1.0 mol.) of 7.3% strength by weight aqueous sodium hypochlorite solution are then added at this temperature and the mixture is stirred at this temperature for 20 minutes. Thereafter, the mixture is heated at 60° C. for 5 minutes. The cyclopropylamine is obtained as an aqueous solution by distillation over a column (163 g). A cyclopropylamine yield of 66%, based on the butyrolactone, is determined by GC analysis and an acid/base titration.

Example 2

Stages (a) and (b): 86.1 g (1.0 mol.) of butyrolactone are heated to a temperature of 135° C., while stirring. 120.0 g (1.6 mol.) of n-butanol and an excess of gaseous hydrogen chloride are metered in over a period of 3 hours, a reaction temperature of 134–138° C. being maintained. During the reaction, 124 g of distillate are removed. The reaction mixture is then freed of excess n-butanol at about 70° C. under a pressure of 60 mbar. A residue of 218.3 g remains.

Stage (c): Methanol is removed from 225.0 g (1.25 mol.) of 30% strength by weight methanolic sodium methylate solution by distillation at a bottom temperature of up to 100° C. The crude chlorobutyric acid butyl ester from stages (a) and (b) is then metered in over a period of 1.5 hours. During this operation, a temperature of 97–100° C. is maintained in the reaction mixture, while a mixture of methanol and n-butanol is removed by distillation continuously. When the metering has ended, the mixture is kept at a bottom temperature of about 100° C. for a further 2 hours.

Stage (d): The reaction mixture of stage (c) is cooled to 60° C. and reacted with an excess of gaseous ammonia under normal pressure. The reaction time is about 5 hours. After cooling to room temperature, the reaction mixture is rendered neutral with 20% strength by weight hydrochloric acid. Solvent residues are removed by distillation over a column at a bottom temperature of up to 120° C. The mixture is allowed to cool and water is added in an amount such that a homogeneous solution (622.4 g) forms. According to HPLC analysis, the cyclopropanecarboxylic acid amide is present in a yield of 73%, based on the butyrolactone.

Stage (e): 160.0 g (2.0 mol.) of 50% strength by weight sodium hydroxide solution are added at 0° C. to the solution from stage (d) and the mixture is heated to about 15° C. 1010.9 g (1.0 mol.) of 7.3% strength by weight aqueous sodium hypochlorite solution are then added to the stage (d) solution at this temperature and the mixture is stirred at this temperature for 20 minutes. Thereafter, the solution is heated at 60° C. for 5 minutes. The cyclopropylamine is obtained as an aqueous solution by distillation over a column (177.0 g). A cyclopropylamine yield of 69%, based on the butyrolactone, is determined by GC analysis and an acid/base titration.

The disclosure of priority German Application No. 198 30 633.4 filed Jul. 9, 1998 is hereby incorporated by reference into the present application.

Obviously, numerous modifications and variations of the present invention are possible in light of the above teachings. It is, therefore, to be understood that within the scope of the appended claims, the invention may be practiced otherwise than as specifically described herein.

What is claimed as new and is desired to be secured by Letters Patent:

1. A process for the preparation of cyclopropylamine from butyrolactone, comprising:

(a) reacting butyrolactone with hydrogen chloride, thereby yielding chlorobutyric acid;

(b) esterifying said chlorobutyric acid with a primary or secondary alcohol having 4–8 carbon atoms;

(c) cyclizing the ester with an alkali metal alcoholate of a primary alcohol having 1–3 carbon atoms without addition of an inert solvent to give a mixture of cyclopropanecarboxylic acid esters;

(d) converting the cyclopropanecarboxylic acid ester mixture into cyclopropanecarboxylic acid amide by reacting the mixture with ammonia; and (e) reacting said cyclopropanecarboxylic acid amide with hypohalite ion in a basic medium, thereby forming cyclopropylamine.

2. The process of claim 1, wherein a chlorobutyric acid ester of a primary, secondary or tertiary alcohol is cyclized with an alkali metal alcoholate of a primary alcohol having 1–3 carbon atoms, thereby yielding the cyclopropanecarboxylic acid ester.

3. The process of claim 2, wherein 1–1.5 equivalents of alkali metal alcoholate are present per equivalent of chlorobutyric acid ester.

4. The process of claim 2, wherein the alkali metal alcoholate is sodium methylate.

5. The process of claim 1, wherein the cyclization reaction is conducted at a temperature from 80–150° C.

6. The process of claim 1, wherein the reaction mixture of the cyclization reaction step (c) is reacted directly with ammonia, without work-up of the medium, to give cyclopropanecarboxylic acid amide.

7. The process of claim 1, wherein the primary alkanol is 1-butanol, 1-pentanol or 1-hexanol and said secondary alkanol is 2-butanol, 2- or 3-pentanol or 2- or 3-hexanol.

8. The process of claim 1, wherein the reaction of butyrolactone with hydrogen chloride occurs at a temperature of 135–140° C. under a pressure of up to 25 bar.

9. The process of claim 1, wherein the reaction of cyclopropanecarboxylic acid ester mixture with ammonia is conducted at a temperature of 40–120° C.

10. The process of claim 1, wherein the amount of hypohalite in step (e) ranges from 1.0–1.5 equivalents and the amount of alkali metal hydroxide ranges from 1.5–2.5 equivalents, each based on the amount of carboxamide reactant.

11. The process of claim 1, wherein the temperature of the reaction of step (e) ranges from 40–150° C.

12. The process of claim 1, wherein said hydrogen chloride and said primary or said secondary alcohol having 4–8 carbon atoms are reacted simultaneously with said butyrolactone.

13. The process of claim 1, wherein said cyclopropanecarboxylic acid ester mixture is reacted with said ammonia within a time of 5–10 hours.

* * * * *